United States Patent
Hoorens

[11] Patent Number: 5,870,785
[45] Date of Patent: Feb. 16, 1999

[54] MAT, MORE SPECIFICALLY A MAT FOR LYING ON

[76] Inventor: Jan Hoorens, Bosstraat 19, B-1702, Dilbeek, Belgium

[21] Appl. No.: 765,408

[22] PCT Filed: Jul. 5, 1995

[86] PCT No.: PCT/BE95/00066

§ 371 Date: Jan. 8, 1997

§ 102(e) Date: Jan. 8, 1997

[87] PCT Pub. No.: WO96/01602

PCT Pub. Date: Jan. 25, 1996

[30] Foreign Application Priority Data

Jul. 11, 1994 [BE] Belgium ................................ 9400647

[51] Int. Cl.⁶ .............................. A47G 9/06; A47C 27/00
[52] U.S. Cl. .................................. 5/652.1; 5/420; 5/724; 442/304; 442/318
[58] Field of Search ........................... 5/724, 652.1, 656, 5/420, 952, 502, 484; 428/119; 442/304, 318

[56] References Cited

U.S. PATENT DOCUMENTS

| | | | |
|---|---|---|---|
| 2,271,281 | 1/1942 | Whitman | 5/502 |
| 3,616,126 | 10/1971 | Tungeath | 4/420 X |
| 3,691,570 | 9/1972 | Gaines et al. | |
| 3,905,057 | 9/1975 | Willis et al. | 428/119 |
| 4,695,496 | 9/1987 | Lee | |
| 5,413,837 | 5/1995 | Rock et al. | 442/318 |
| 5,552,205 | 9/1996 | Lea | 5/420 X |
| 5,651,847 | 7/1997 | Loeffler | 442/418 |

FOREIGN PATENT DOCUMENTS

| | | |
|---|---|---|
| 0261904 | 3/1988 | European Pat. Off. |
| 2616320 | 12/1988 | France |
| 2851348 | 7/1979 | Germany |
| 9112275 | 1/1992 | Germany |
| 4111743 | 10/1992 | Germany |
| 455142 | 6/1968 | Switzerland |

*Primary Examiner*—Michael F. Trettel
*Attorney, Agent, or Firm*—Browdy and Neimark

[57] ABSTRACT

A mat for a person to lie on has an air-permeable top layer (1), a bottom layer (2), and a middle layer (3) which includes an open three-dimensional knitted structure with mesh openings (5) in the top layer, which is of an open-mesh, air-permeable fabric. The structure is formed of evenly-spaced, substantially rigid monofilaments (4, 4') between the top and bottom layers. The middle layer is substantially incompressible a person's weight. In the middle layer air occupies at least five times the volume of the monofilaments and because of the open knitted structure air can flow through the middle layer and the top layer. The filaments preferably include both perpendicular monofilaments (4) and cross-over monofilaments (4') which can brace diagonally across the mesh openings (5). The monofilaments are preferably woven into the top and/or bottom layers.

20 Claims, 2 Drawing Sheets

MAT, MORE SPECIFICALLY A MAT FOR LYING ON

The invention concerns a mat, more specifically a mat for lying on, which for example is to be laid on top of a mattress or on a hard surface, such as a floor, with an air-permeable top layer and a bottom layer facing it, separated from each other by a middle layer with an open structure.

According to the invention, the aim is among other things to propose a mat which makes it possible to prevent overheating of those parts of the body in contact with the mat, in particular during hot weather, and more specifically in the case of bed-ridden persons and babies.

Further, the invention also aims to propose a mat which makes it possible to considerably reduce the risk of suffocation or cot death in babies.

To this end, the mat according to the invention comprises a three-dimensional knitted structure, with a middle layer essentially formed by open, relatively rigid threads, more specifically monofilaments, where said threads form part of said three-dimensional knitted structure, and where said threads, more or less evenly distributed, are placed at a certain distance from each other, such that a) said middle layer is more or less incompressible under the weight of a person lying on the top layer, and b) a permanent flow of air is possible between said middle layer and the top layer.

The top and bottom layers are purposefully parallel to each other, and at least 70% of the monofilaments in the middle layer extend more or less perpendicularly to said top and bottom layers, with the remaining portion of the monofilaments being crossed over each other and distributed over the middle layer, in order to prevent said perpendicular monofilaments from turning over or bending under the weight of a person lying on top of the mat.

In an advantageous embodiment of the invention, at least the above-mentioned top layer consists of a knitted structure with meshes having a cross-section of 0.5 mm to 10 mm, and preferably a cross-section of between 2 and 4 mm.

Other features and advantages of the invention will be apparent from the following description of some specific embodiments of a mat for lying on according to the invention; this description is given by way of example and in no way limits the scope of the protection afforded. The reference numbers used below relate to the accompanying drawings.

Figure 3:
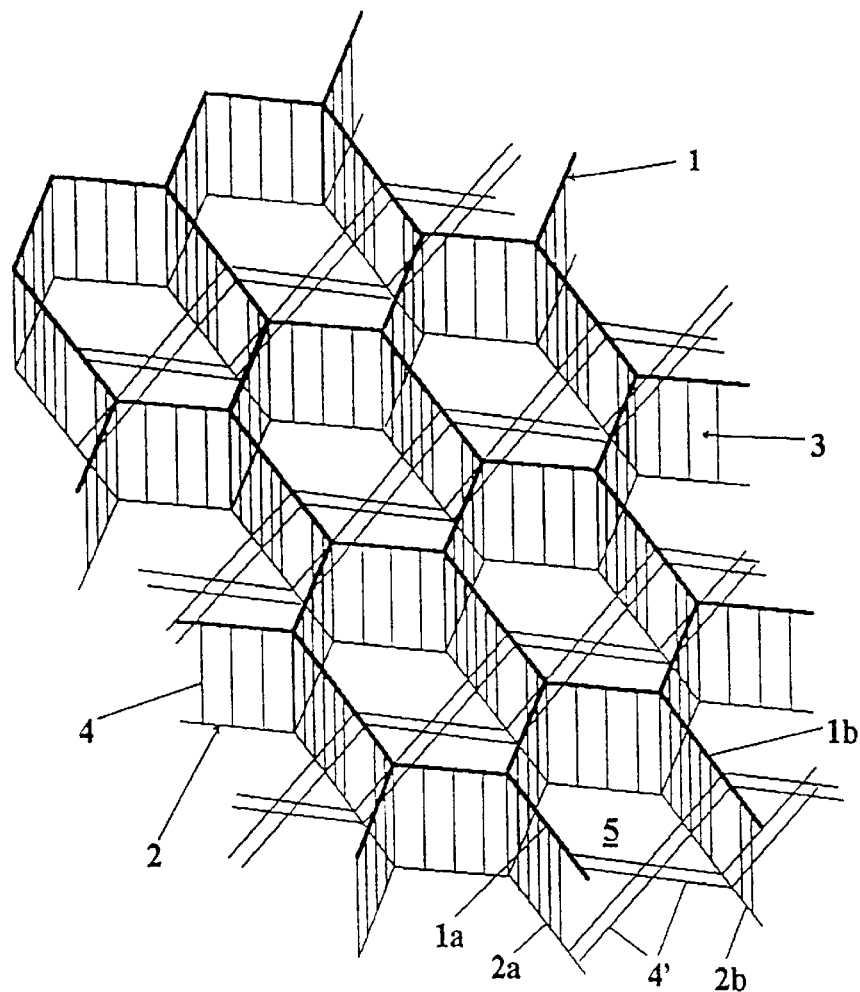

FIG. 3, on a greater scale, is a schematic perspective view of part of a mat for lying on according to a third embodiment of the invention.

Figure 4:
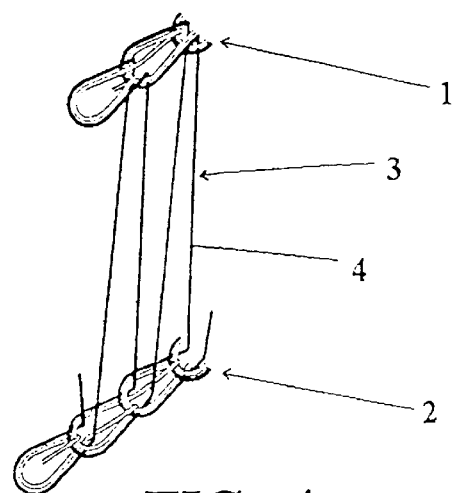

FIG. 4, on an even greater scale, is a schematic detail representation of a special component of the mat according to FIG. 3.

In these drawings, the same reference numbers refer to identical or analogous elements.

The mat for lying on presented in the drawings essentially comprises a three-dimensional knitted structure ("Abstandsgewirke"-"face-to-face fabric") with a top layer 1 and a bottom layer 2 separated from each other by a middle layer 3.

At least the top layer 1 and the middle layer 3 are permeable to air, such that an air flow can arise through the top layer 1 and the middle layer 3, more specifically from the middle layer 3 through the top layer 1. In the middle layer 3, the air flow can occur over the entire mat, in all directions. The continuous ventilation thus generated also ensures that the person lying on top of the mat does not suffer from perspiration.

A baby lying with its face on the mat will always receive a sufficient supply of air through the middle layer 3 and the top layer 1 of the mat, so that the risk of suffocation is virtually excluded and furthermore better temperature regulation is possible.

In the middle layer 3 in particular, the amount of free space is very great in comparison to the material from which said layer is formed, and its volume is preferably at least five times the volume of said material.

Figure 1:
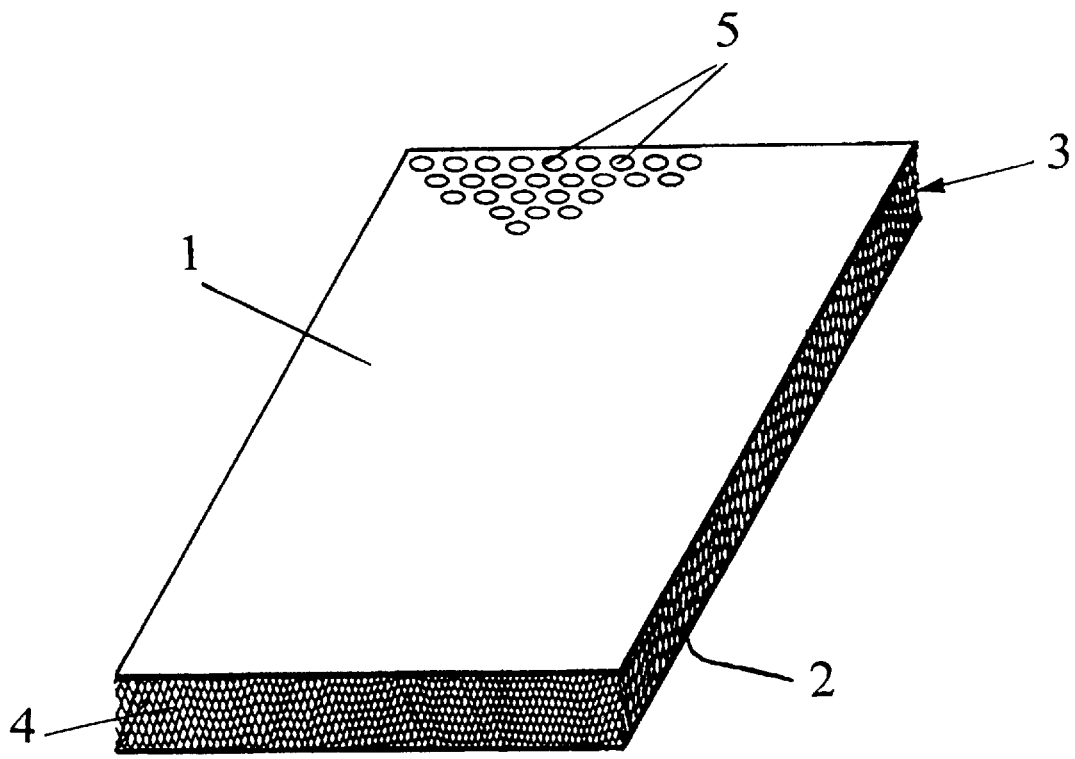
FIG. 1 is a schematic perspective view of part of a mat for lying on according to a first embodiment of the invention.

In the specific embodiment as represented in FIG. 1, the middle layer 3 comprises upright threads 4 woven into those of the top layer 1 and the bottom layer 2. These extend obliquely with respect to the top and bottom layers 1 and 2 which are parallel to each other; said upright threads make the same angle when crossing each other or the two layers, in order to give the middle layer sufficient springiness in a direction perpendicular to it, and at the same to give the required rigidity to ensure that said middle layer is not compressed under the weight of the person lying on top of the mat, thus maintaining the above-mentioned airflow.

To this end, said threads 4 consist for example of relatively rigid monofilaments, preferably with a diameter in the order of 0.01 mm to 0.5 mm, more specifically between 0.09 mm and 0.21 mm.

The middle layer 3 can mostly have a thickness of between 0.1 cm and 1 cm, but preferably between 0.3 and 0.6 cm, for example 0.45 cm.

The top layer 1 consists of an open fabric or knitted structure with sufficiently large meshes 5, which ensure the through-flow of air. These preferably have a diameter between 0.5 mm and 10 mm, more specifically between 2 and 4 mm.

The bottom layer 2 is preferably impermeable to moisture. This is particularly important if the mat for lying on is used on a damp surface or as a mattress protector. To this end, the bottom layer 2 can for example consist of a densely woven or knitted structure, on to which a film of plastic or aluminium can be laminated or glued.

Figure 2:
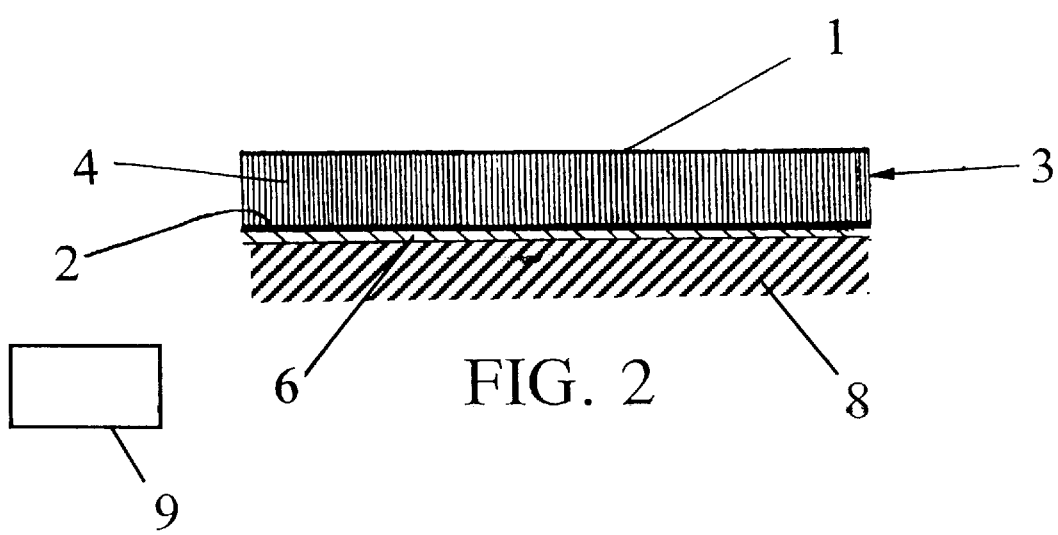
FIG. 2 represents a schematic cross-section of part of a mat for lying on according to a second embodiment of the invention.

The embodiment shown in FIG. 2 differs from that in FIG. 1 in that the middle layer 3 consists of relatively thick, rigid, upright monofilaments 4, which are not crossed and extend more or less perpendicularly to the top and bottom layers 1 and 2.

Further, the bottom layer 2 consists of a moisture-absorbing material, to the outside of which is glued a plastic film 6 which ensures that the bottom of the mat for lying on is moisture-proof. FIG. 2 also shows the pad removably attached to a mattress 8, and means 9 for creating a forced air flow through the top layer 1 via the middle layer 3.

In the preferred embodiments according to FIGS. 1 and 2, the middle layer 3 consists of synthetic monofilaments 4, such as polyester with a diameter of 0.08 mm, while the top layer 1 consists essentially of cotton (detex 100/1) and the bottom layer 2 consists of a polyester fabric (detex 110).

FIGS. 3 and 4 relate more specifically to a special embodiment of the three-dimensional knitted structure which according to the invention forms the main part of the mat.

As can be seen, both the top layer 1 and the bottom layer 2 are formed by a very open meshwork, whose meshes 5 are hexagonal.

Further, the meshes 5 of both layers are directly opposite each other, and the corresponding sides of said meshes are connected with each other by monofilaments 4, of which at least 70% and preferably at least 90% extend perpendicularly to the two layers 1 and 2 and determine the middle layer 3. The remaining monofilaments are crossed over each other and are evenly distributed over the whole volume of the middle layer 3.

For the sake of clarity, said remaining monofilaments are indicated in FIG. 3 by reference number 4'.

As can be clearly seen on this figure, said oblique crossed monofilaments 4' connect one side 1a of each of the meshes 5 of the top layer 1 with a side 2b of the bottom layer 2 located under the side 1b of the top layer lying opposite, and conversely connect the side 1b of the top layer 1 with the side 2a of the bottom layer 2.

In this way, the upright monofilaments 4 are prevented from bending or turning over under the weight of a person lying on top of it, thus making the mat more or less incompressible under such a weight.

Furthermore, in order to obtain a stable whole, the monofilaments 4 and 4' form part of the three-dimensional knitted structure itself, and are in a way woven into the sides of the layers 1 and 2 which delimit the meshes 5. In this way the three layers 1, 2 and 3 are formed in a single knitting pass.

Also, the sections of the monofilaments 4 and 4' which are woven into the top and bottom layers 1 and 2 are completely sunk into said layers, such that the outsides of both these layers are nearly completely smooth.

This is illustrated in FIG. 4, which is a schematic representation of part of a side of one of the meshes of the top layer 1 and of part of the corresponding side underneath it in the bottom layer 2.

Further, at least the top layer 1 consists essentially of microfilaments which themselves are known. For the sake of clarity, however, these microfilaments are not shown in FIG. 4.

In the embodiment according to FIGS. 3 and 4, the three-dimensional knitted structure corresponds to the following specifications:

top layer 1: microfilaments of polyester dtex 110f 128×3; JET-TEX (trademark of Hoechst)

middle layer 3: monofilaments of polyester with diameter of 0.16 mm bottom layer 2: polyester dtex 167 f 32×1.

In some cases, means may be easily provided to obtain a forced air flow through the top layer 1 via the middle layer 3. This can be done for example by connecting a dismountable fan on one of the edges of the mat by means of a suitable nozzle which extends over the full length of the side and is attached to it by means of a clamp system without compressing the mat.

In addition to the above-mentioned advantages, the mat according to the invention has the further advantage that it is easy to wash, due in particular to the more or less continuous free space of the middle layer 3.

Further, this mat remains free of house mites, thanks to the above-mentioned continuous flow of air in the middle layer 3, the relatively low temperature which is maintained and the absence of perspiration moisture, making it ideal for people who are allergic to these mites.

Further, the three-dimensional knitted structure shown in FIG. 3 is very easy to see through, thanks to the meshes lying opposite each other in the top and bottom layers, making it easy to check the permeability to air.

These different types of three-dimensional knitted structure can be manufactured by the "Karl Mayer" company using a machine of the type "RD-6".

The invention is of course in no way limited to the embodiments described above and shown in the accompanying drawings; other variants can be considered as regards the choice of material used for the knitted structure and the dimensions of same.

Further, the mat can for example form part of the top of a mattress, being removably attached to the mattress. The thickness and rigidity of the mat can also be varied in function of the weight of the person lying on top of it.

On at least one of the layers 1 or 2, but preferably on the top layer 1, an extra molton layer may be provided, such that the air-permeability of the top layer is scarcely affected.

Finally, the invention is not limited to a mat for lying on but can be applied wherever there are problems of cooling, air permeability, oxygen supply, etc., such as for horse blankets or saddle cloths.

I claim:

1. A mat, for a person to lie upon, comprising an air-permeable top layer (1), a bottom layer (2) facing thereto, and a middle layer (3) between the top layer and the bottom layer, wherein the middle layer comprises:

an open three-dimensional knitted structure of substantially rigid monofilaments (4,4'), the monofilaments extending generally transverse to the top layer and the bottom layer and being generally evenly spaced at a predetermined distance from one another; wherein the top layer comprises an open-mesh, air-permeable fabric, the middle layer is substantially incompressible under the weight of the person lying on the top layer, and an air-filled free space in the middle layer occupies at least five times a volume of the monofilament in the middle layer;

whereby air is flowable through the middle layer and the top layer.

2. The mat according to claim 1, wherein the monofilaments (4) and (4') have a diameter of between 0.01 mm and 0.5 mm.

3. The mat according to claim 2, wherein the diameter is between 0.09 mm and 0.21 mm.

4. The mat according to claim 1, wherein said middle layer (3) has a thickness of between 0.1 cm and 1 cm.

5. The mat according to claim 1, wherein at least said top layer (1) includes a knitted structure with meshes (5) of 0.5 mm to 10 mm in cross-section.

6. The mat according to claim 4, wherein the thickness is between 0.3 cm and 0.6 cm.

7. The mat according to claim 5, wherein the meshes are of between 2 mm and 4 mm cross-section.

8. The mat according to claim 13, wherein portions of the monofilaments comprise a part of the top layer (1) and a part of the bottom layer (2) and are sunk into the top layer and the bottom layer.

9. The mat according to claim 1, wherein at least the top layer (1) includes microfilaments.

10. The mat according to claim 1, wherein a molton layer is provided on at least one of the mat's outside surfaces.

11. The mat according to claim 1, wherein a moisture-proof film (6) is applied to the bottom.

12. The mat according to claim 1, wherein the mat forms part of a mattress and is removably attached to the mattress.

13. The mat according to claim 1, wherein means are provided for creating a forced air flow through the top layer (1) via the middle layer (3).

14. The mat according to claim 1, wherein the transverse monofilaments comprise perpendicular monofilaments (4)

and cross-over monofilaments (4'), whereby the perpendicular monofilaments are prevented from turning over or bending under a weight of the person.

15. The mat according to claim 1, comprising mesh openings (5) between about 0.5 mm and about 10 mm across, wherein
   the open three-dimensional knitted structure further comprises perpendicular monofilaments (4) extending between the top layer and the bottom layer in areas outside of the mesh openings, and
   the monofilaments are evenly spaced in the areas outside of the mesh openings.

16. The mat according to claim 15, comprising cross-over monofilaments (4') obliquely connecting the top layer and the bottom layer across the mesh openings.

17. The mat according to claim 16, wherein a ratio of cross-over monofilaments to perpendicular monofilaments is between approximately 1:9 and approximately 3:7.

18. The mat according to claim 15, wherein the mesh openings are generally hexagonal.

19. The mat according to claim 1, wherein
   the perpendicular monofilaments are woven into the top layer and the bottom layer.

20. The mat according to claim 1, wherein the perpendicular monofilaments are inclined obliquely to the top layer and the bottom layer.

* * * * *